United States Patent
Burgermeister et al.

(10) Patent No.: US 8,518,052 B2
(45) Date of Patent: Aug. 27, 2013

(54) MEDICAL DELIVERY SYSTEM FOR DELIVERY OF A MEDICALLY USEFUL PAYLOAD

(75) Inventors: Robert Burgermeister, Bridgewater, NJ (US); Matthew E. Krever, Warren, NJ (US); Ramesh V. Marrey, Basking Ridge, NJ (US); Daniel Olsen, Califon, NJ (US)

(73) Assignee: Cordis Corporation, Miami Lakes, FL (US)

( * ) Notice: Subject to any disclaimer, the term of this patent is extended or adjusted under 35 U.S.C. 154(b) by 1143 days.

(21) Appl. No.: 11/488,401

(22) Filed: Jul. 18, 2006

(65) Prior Publication Data

US 2007/0162101 A1 Jul. 12, 2007

Related U.S. Application Data

(60) Provisional application No. 60/757,123, filed on Jan. 6, 2006.

(51) Int. Cl.
*A61F 11/00* (2006.01)
(52) U.S. Cl.
USPC .......................... 606/108; 600/141; 623/1.11
(58) Field of Classification Search
USPC ..... 606/108, 1, 110, 119, 127–129, 144–147, 606/159, 167–180, 190–200; 623/1.11; 604/164.06, 95.04, 523, 525, 528; 600/101, 600/104, 136, 139, 140, 141, 142, 143, 146, 600/373
See application file for complete search history.

(56) References Cited

U.S. PATENT DOCUMENTS

| | | | |
|---|---|---|---|
| 4,911,148 A * | 3/1990 | Sosnowski et al. | 600/136 |
| 5,041,126 A | 8/1991 | Gianturco | |
| 5,242,721 A * | 9/1993 | Oonuki et al. | 428/34.5 |
| 5,397,321 A * | 3/1995 | Houser et al. | 606/41 |
| 5,454,787 A | 10/1995 | Lundquist | |
| 5,477,856 A * | 12/1995 | Lundquist | 600/373 |
| 5,843,153 A | 12/1998 | Johnston | |
| 6,056,775 A | 5/2000 | Borghi | |
| 6,132,390 A | 10/2000 | Cookston et al. | |

(Continued)

FOREIGN PATENT DOCUMENTS

| | | |
|---|---|---|
| EP | 0508473 | 10/1992 |
| EP | 0508473 B1 | 10/1992 |

(Continued)

OTHER PUBLICATIONS

International Search Report re: PCT/US2007/060243 dated Jul. 30, 2007.

(Continued)

*Primary Examiner* — Ryan Severson
*Assistant Examiner* — David Eastwood

(57) ABSTRACT

The present disclosure concerns a delivery system for delivering a medically useful payload through the vasculature to a site of interest in the patient's body. The medically useful payload may be a therapeutic device, such as a stent, and it may be a diagnostic tool, such as an imaging device. Owing to its structural attributes, the presently-inventive delivery system is well suited for carrying medical payload to and through vessel curvature and to branched regions (i.e., bifurcations) in same. Also, the device is well-suited to traveling through a vessel over a guiding element, such as a guidewire, which itself exhibits curvature.

3 Claims, 15 Drawing Sheets

(56) References Cited

U.S. PATENT DOCUMENTS

| | | | |
|---|---|---|---|
| 6,139,753 A | 10/2000 | Taylor | |
| 6,187,034 B1 | 2/2001 | Frantzen | |
| 6,246,914 B1 * | 6/2001 | de la Rama et al. | 607/122 |
| 6,544,218 B1 | 4/2003 | Choi | |
| 6,869,414 B2 | 3/2005 | Simpson | |
| 6,907,298 B2 * | 6/2005 | Smits et al. | 607/125 |
| 6,939,338 B2 | 9/2005 | Waldhauser | |
| 6,979,319 B2 | 12/2005 | Manning | |
| 7,018,372 B2 | 3/2006 | Casey et al. | |
| 7,022,131 B1 | 4/2006 | Derowe | |
| 7,269,453 B2 * | 9/2007 | Mogul | 600/374 |
| 7,351,214 B2 | 4/2008 | Burgermeister | |
| 2001/0049549 A1 | 12/2001 | Boylan | |
| 2003/0105415 A1 | 6/2003 | Mirigian | |
| 2004/0006305 A1 * | 1/2004 | Hebert et al. | 604/96.01 |
| 2004/0225183 A1 * | 11/2004 | Michlitsch et al. | 600/106 |
| 2004/0254450 A1 | 12/2004 | Griffin et al. | |
| 2005/0049667 A1 | 3/2005 | Arbefeuille | |
| 2006/0074308 A1 * | 4/2006 | Rafiee et al. | 600/435 |
| 2006/0074372 A1 | 4/2006 | Haga et al. | |
| 2007/0270781 A1 | 11/2007 | Burgermeister | |
| 2008/0319418 A1 * | 12/2008 | Chong | 604/528 |

FOREIGN PATENT DOCUMENTS

| | | |
|---|---|---|
| EP | 0778040 | 6/1997 |
| EP | 1101455 | 5/2001 |
| EP | 1101455 B1 | 5/2001 |
| FR | 2713492 A1 | 6/1995 |
| JP | 2-1292 | 1/1990 |
| JP | 5-501065 | 3/1993 |
| JP | 5-177002 | 7/1993 |
| JP | 6-23031 | 2/1994 |
| JP | 10-85337 | 10/1998 |
| JP | 2001510083 | 7/2001 |
| JP | 2002527179 | 8/2002 |
| JP | 2004180764 | 7/2004 |
| JP | 2005-125101 | 10/2004 |
| WO | WO 90/10417 A1 | 9/1990 |
| WO | WO 96/39999 | 12/1996 |
| WO | WO 96/39999 A1 | 12/1996 |
| WO | WO 99/03722 A1 | 1/1999 |
| WO | WO 99/62415 | 12/1999 |
| WO | WO 00/22981 A1 | 4/2000 |
| WO | WO 03/002037 | 1/2003 |
| WO | WO 03/002037 A1 | 1/2003 |
| WO | WO 2007/035471 A2 | 3/2007 |

OTHER PUBLICATIONS

Final Rejection issued by the USPTO for corresponding U.S. Appl. No. 11/621,047 dated Oct. 25, 2010.

Non-Final Rejection issued by the USPTO for corresponding U.S. Appl. No. 11/621,047 dated May 12, 2010.

Final Rejection issued by the USPTO for corresponding U.S. Appl. No. 11/621,047 dated Oct. 2, 2009.

Requirement for Restriction/Election issued by the USPTO for corresponding U.S. Appl. No. 11/621,047 dated Apr. 7, 2009.

Non-Final Rejection issued by the USPTO for corresponding U.S. Appl. No. 11/621,047 dated Jul. 28, 2008.

Office Action issued by the Japanese Patent Office for corresponding Application No. 2008-549677, dated Oct. 18, 2011.

Office Action issued by the Australian Patent Office for corresponding Application No. 2007204738, dated Sep. 5, 2011.

Office Action issued by the European Patent Office for corresponding Application No. 07252634.6, dated Jan. 27, 2011.

Office Action issued by the European Patent Office for corresponding Application No. 07252634.6, dated Aug. 23, 2011.

European Search Report for corresponding Patent Application No. 07252634.6-1257/1892008 dated Jul. 21, 2009.

International Search Report for corresponding Patent Application No. PCT/US2007/060243 mailed Jul. 30, 2007.

Japanese Notification of Reasons for Refusal, dated Feb. 14, 2012, in corresponding application Japanese Application No. 2007-186011.

Japanese Notification of Reasons for Refusal, dated Oct. 18, 2011, in related application Japanese Application No. 2008-549677.

* cited by examiner

Single region of high axial stiffness
relative to rest of circumference

Single region of low axial stiffness
relative to rest of circumference

Regions of high
axial stiffness
180 degrees apart

Regions of high and
low axial stiffness
alternating at 90
degree orientations

Regions of low axial stiffness 180 degrees apart

Low axial stiffness

Axial stiffness increasing from low to high

High axial stiffness

MEDICAL DELIVERY SYSTEM FOR DELIVERY OF A MEDICALLY USEFUL PAYLOAD

CROSS REFERENCE TO RELATED APPLICATION

This application is related to U.S. provisional patent application No. 60/757,123, filed Jan. 6, 2006, now pending.

FIELD OF THE INVENTION

The present disclosure concerns a delivery system for delivering a medically useful payload through a channel in the patient's body, such as the vasculature, to a site of interest. The medically useful payload may be a therapeutic device, such as a stent, and it may be a diagnostic tool, such as a camera. Owing to its structural attributes, the presently-inventive delivery system is well suited for carrying medical payloads to and through vessel curvature and to branched regions (i.e., bifurcations) in same. Also, the device is well-suited to traveling through a vessel over a guiding element, such as a guidewire, which itself exhibits curvature.

BACKGROUND OF THE INVENTION

Diseases of the vasculature, such as stenoses, strictures or aneurysms in blood vessels and other body vessels can be treated by the implanting a payload, such as a stent, graft, or the like, at the site of disease. Such payload can be carried to the site of implantation by a delivery device having a catheter for carrying and deploying the payload. The catheters can be expected to carry the payload over a relatively long distance, often from an incision in the patient's groin area, through the vasculature, to a location where action is required. For example, a site in the vicinity of the patient's heart may be the target for payload deployment.

From incision to deployment site, the path is defined by the interior of a vessel that the catheter must travel. The vessel may have segments that are difficult to traverse. Curves or bifurcations in vessels exemplify two particular kinds of segments that can present such difficulties. Likewise, the deployment site may be curved, or a bifurcation may be present at the site of deployment.

A bifurcation in a vessel is a location where the vessel divides into two branches or parts. The vessel bifurcations generally have circumferential asymmetry. That is, bifurcated vessels generally exhibit asymmetry around their circumference at the point where the main vessel divides into one or more branches. Thus, the opening in the side branch vessel where the side branch vessel joins the main branch vessel may be asymmetrical. The side branch vessel may join the main branch vessel at an oblique angle, which may contribute to the asymmetry of the bifurcation cross-section.

One kind of prior art bifurcation delivery device employs multiple guidewires and/or the clinician to orient and manipulate the device relative to the bifurcation. For example, attempts have been made to accomplish this solely through the use of two wires or wire-like elements (one in each branch of bifurcation) to force rotation of the device to match the vessel anatomy. This approach has shortcomings. First, by requiring delivery of the medical device to the location of the bifurcation over two wires (for substantially the entire delivery), the chance of wire wrapping is greatly increased. This prevents complete delivery of the device and can result in the clinician having to withdraw a wire and rewire the vessels, causing significant procedural delay and patient risk. Second, reliance on two wires for device orientation is typically insufficient to guarantee full and proper alignment of the entire medical device with the side branch ostium (particularly the portion of the device proximal to the carina (or apex) of the bifurcation) Even when both branches of the bifurcation are wired and the medical device is seated on the carina, the wires are not able to exert enough rotational influence on the device to align the whole length of the payload.

In any event, carrying the payload through a vessel curvature, a bifurcation, or otherwise deploying the payload at such locations can present challenges in terms of traversing or accessing the site. Furthermore, where the payload needs to be in a specific orientation (such as for maximizing the therapeutic effect or diagnostic purpose of the payload), achieving the desired orientation in such curvature or bifurcation presents yet another challenge to the person of skill in the art.

U.S. Pat. No. 6,544,218, entitled "Catheter With Biased Shaft" is disclosed as a reference of interest.

SUMMARY OF THE INVENTION

The present invention is directed to a flexible catheter for the delivery of a medically useful payload to a target site within a patient's body. By way of example, the medically useful payload may be a stent, or it could be an atherectomy member. In these instances, the medically useful payload is delivered to a site of disease within a blood vessel of a patient. In yet other examples the medically useful payload may be a camera, a light, or both, which can be carried to a site where observation is warranted for purposes of making a medical diagnosis. In one aspect of the present invention, a flexible region is located at a distal end of the delivery device, which flexible region exhibits a preferential bending direction. That is, the structure of the flexible region permits bending in substantially only one direction. The flexible distal region can curve or bend in a preferred direction that permits the device to bend in accordance with the shape of the vessel or guidewire (if possessing a curved segment) on which the delivery device may be tracked.

Thus, the delivery device of the present invention is adapted to deliver medical payloads (such as stents) to vessels that are curved and/or bifurcated, or other vessel configurations, such as those with eccentric lesions, that are better serviced by deploying oriented devices. That is, there are occasions where the device should be oriented in a specific fashion relative to the bifurcation, curvature, or other vessel feature, or even oriented in response to a bend in the guidewire. Such orientation can be achieved with the present invention.

In another aspect of the present invention, the unidirectional bending member with preferred bending direction is distally located on the delivery device and is coupled thereto to allow a degree of torsional movement of the unidirectional bending member, relative to other parts of the device. That is, the unidirectional bending member is attached to the delivery device in a manner that allows the unidirectional bending member to rotate as necessary to orient the member and conform the distal end of the device, where the member is located, to the shape of the vasculature, in order to deploy or carry the payload so the payload can be properly oriented.

In a further aspect of the present invention, the payload can be co-located with the unidirectional bending member. For example, a stent can be positioned in or over the unidirectional bending member. In an alternative arrangement, the payload is not co-located with the unidirectional bending member, yet is coupled to the unidirectional bending member through sufficient intervening structure so as to undergo orientation in response to the orientation of the unidirectional bending member.

In a specific aspect of the present invention, the unidirectional bending member, owing to its structural attributes and/or construction, can bend in substantially only one direction. A structural arrangement of this kind can result from providing only one member segment or side that the member can bend around. This particular member segment or side becomes the interior, or short side, of the bend.

In a more specific aspect of the present invention, another bending member side, most likely positioned opposite from the bending member side which the member is capable of bending around may be provided with a structural attribute that allows that member segment to function as the outer side which the member bends around. This particular member segment or side becomes the exterior, or long side, of the bend.

A member cut into a plurality of segments, wherein the adjacent segments on one side of the member are connected to each other, and wherein the segments are not interconnected on the side opposite the connections, exhibits bending in substantially only one direction. The interconnected side would be the interior, or short side of the bend (with the member bending around the interconnections) and the open side would be on the exterior, or long side, of the bend.

In the aforedescribed arrangement, the member can bend substantially in only one direction, that is, around the interconnections. The interconnections are sufficiently stiff so as to prevent the member from bending in a manner in which the interconnections are positioned on the long side of the bend. Thus, the member can bend in substantially only one direction. It should be understood that the universal bending member of the present invention could be solid, and it also may be tubular. Tubular arrangements may be easier to fabricate, and further, can move along or otherwise be positioned over a guiding element, such as a guidewire. Thus, in certain arrangements, tubular unidirectional bending members may be preferred.

The substantially unidirectional bending characteristic of the unidirectional bending member of the present invention facilitates orientation of the device as it travels through (1) curves or bifurcations in the vessel, (2) curves or bends in the guidewire, or (3) other eccentricities located within the vessel that force the member into a curved path. So long as the unidirectional bending member possesses a sufficient degree of freedom to rotate, it will assume the path of least resistance in the course of its travels, and thereby rotate/orient itself to conform to the bend in the vessel. Thus, by linking or associating a payload with the unidirectional bending member, orientation of the payload can be attained as a result of the orienting action undertaken by the unidirectional bending member.

Aside from being adapted to pass relatively easily through bends and curves in the vasculature, the self-orienting unidirectional bending member can be used in a number of beneficial ways. Stents deployed at the site of or in the vicinity of a bifurcation may have asymmetrical design features intended to conform to the bifurcation, and in particular, the side branch ostium. Such stents must be deployed in the proper orientation, a result that can be obtained by coupling such stents to the unidirectional bending member, and then allowing the member to orient itself in the vessel. Likewise, a camera or other diagnostic tool, such as an ultrasound transducer (IVUS), pressure transducer, infrared sensor, endoscope lens coupled to the unidirectional bending member could be properly oriented as a result of unidirectional bending member orientation. Furthermore, the self-orienting nature is useful where the bend, so to speak, is imparted by the guidewire which passes through the catheter. For instance, the unidirectional bending member may travel over a guide wire passed into a bifurcation side branch, allowing a stent to be deployed, in its proper orientation, in the side branch. In yet another example, a guidewire having a prebent section can be used to effect orientation of the unidirectional bending member in situations where vessel characteristics are not of an orientation-producing nature. In other words, by positioning the bend in the guidewire at the desired location, the unidirectional bending member will orient itself as it traverses the bend. This arrangement is advantageous where it is desirable to achieve orientation in a relatively straight vessel segment. In any event, with these arrangements, rotation of the unidirectional bending member for positioning of payload, whether for deployment or other medically useful purpose is facilitated. Further, it should be understood that with the unidirectional bending member of the present invention, it is not just the payload which is properly oriented. For example, in the case of a bifurcated vessel, the side branch guidewire exit port can be oriented to face the ostium of the side branch vessel. In other words, as the unidirectional bending member rotates, the side branch guidewire exit port aligns according to the unidirectional bending member orientation, with the side branch guidewire element facing the side branch ostium. This arrangement makes it possible for the unidirectional bending member to properly orient to the side branch anatomy when the device is seated at the carina of the bifurcation. This arrangement also makes it easier for the side branch guide wire to be advanced out of the delivery catheter and into the side branch.

The flexible portion of the delivery device can be constructed a number of other ways. For example, the directional mechanical properties of a material can be manipulated in order to increase flexibility in desired locations about the circumference of the unidirectional bending member. As an alternative, the material properties can be distributed around the circumferential direction of the delivery device, thereby creating a preferred bending direction. The geometry of a structure can also be altered in order to create flexibility in the preferential direction of the bend. As will be explained in the detailed description of the invention, there are a number of ways to attain a preferred bending direction, and in particular, a unidirectional bending direction, in a delivery device component.

Chemical, electrical/thermal or mechanical means can be used to modify unidirectional bending member stiffness so the unidirectional bending member can be transversely displaced, resulting in a preferred bending orientation. For example, the unidirectional bending member may be provided with a substantially unidirectional bend by the manual placement or displacement of a stiffening material within the unidirectional bending member. The unidirectional bend may be effected by thermally modifying at least one portion of the unidirectional bending member. The unidirectional bend may be effected by chemically modifying at least one portion of the unidirectional bending member. The unidirectional bend may be effected by electrically inducing a variation in material phase change, change in modulus, or change in yield stress in the unidirectional bending member.

DETAILED DESCRIPTION OF THE INVENTION

Figure 1:
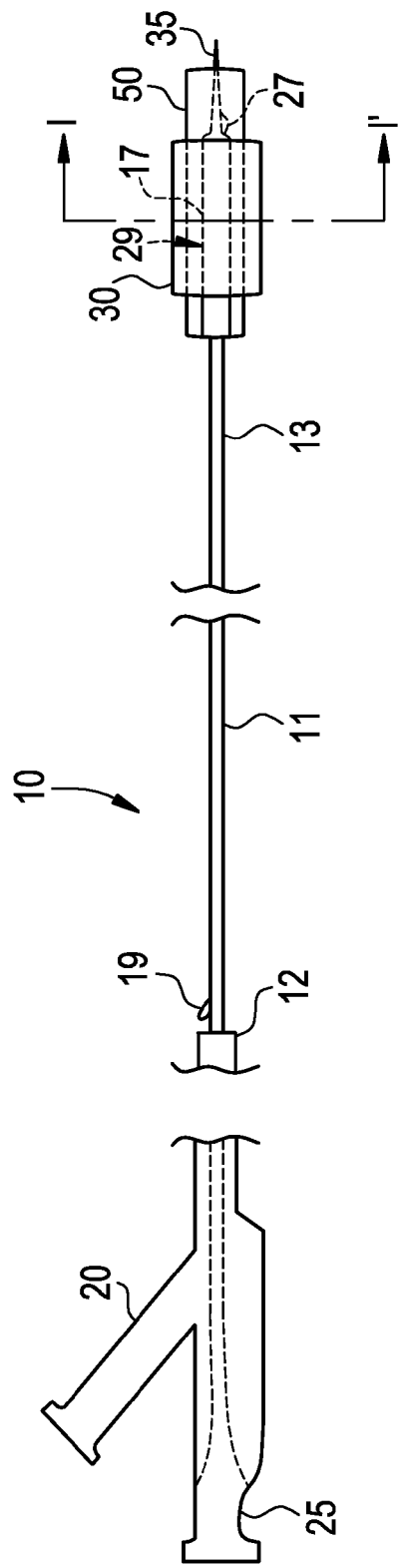
FIG. 1 is a perspective view of a device of the present invention.
Figure 2:
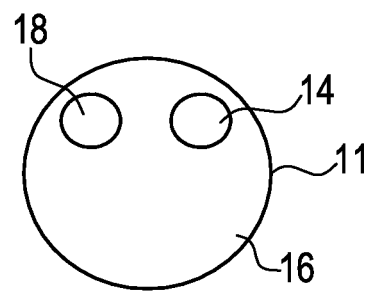
FIG. 2 is a cross sectional view of an aspect of the present invention.

FIGS. 1 and 2 illustrate a catheter 10 of the kind suitable for treating bifurcations in which the payload is a balloon expandable stent. Catheter 10 includes an inflatable balloon and therefore is useful for deploying a balloon expandable stent, although it should be understood that the delivery system described herein could be employed with a self expanding stent, obviating the need for an inflation balloon and lumen to transport inflation fluid (it should be noted that if the payload were an self expanding stent, such as one manufactured of the nitinol material, then the device would require a outer restraining sheath positioned over the stent). Catheter 10 generally comprises an elongated catheter shaft 11 having a proximal end 12, a distal end 13, At least one guidewire lumen 14 is adapted to receive and pass a guidewire, though a second guidewire lumen 18 is depicted here. An inflation port 20 at the proximal end of catheter shaft 11 has an opening for receiving an inflation fluid from an external source. The inflation port is in fluid communication with the open annular space 16 present within shaft 11. Guidewire entry port 25 is found at the proximal device end, and can be in communication with guidewire lumen 14 or 18 that are discussed below. An RX guidewire lumen port 19 is located between proximal and distal ends 12 and 13 as shown in FIG. 1. RX guidewire lumen port 19 is in communication with the other of the guidewire lumens 14 or 18.

In the embodiment of FIG. 1, the shaft 11 is a multiple-lumen shaft, typically extruded or otherwise formed with at least one guidewire lumen 14, and possibly second guidewire lumen 18 present in annular space 16. Annular space is sealed on its exterior by wall of shaft 11 and therefore serves as the conduit for transferring the balloon inflation fluid. Here, where the device is intended for the delivery of a stent, at the site of a bifurcation, it is advantageous, though not entirely necessary, to employ a catheter that can receive and pass at least two guidewires 32 and 33. The catheter shaft is provided with lumens for main branch and side branch guidewires, such lumens designated 14 and 18, respectively.

Figure 3:
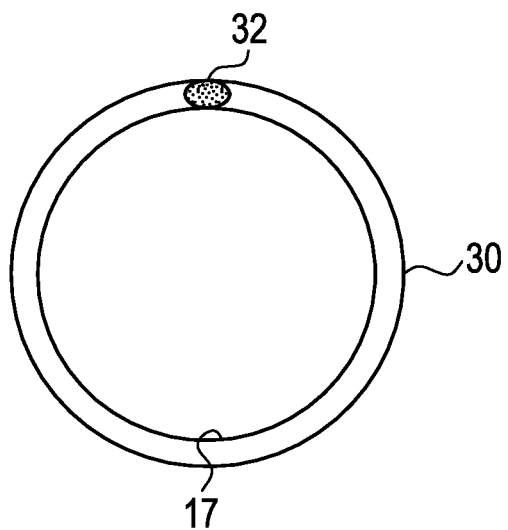
FIG. 3 is a cross sectional view of another aspect of the present invention.

The distal end of the annular space 16 is proximal to the distal end of the guidewire lumens 14 and 18. An inflatable balloon 17 is disposed on a distal section of catheter shaft 11, having a proximal end and a distal end is secured and sealed to the shaft 11. The opening in the balloon at its proximal end is in fluid communication with annular space 16 so that the balloon can receive and retain the inflation fluid as it flows from the external source, through inflation port 20, through annular space 16, and into balloon 17. A stent 30 is mounted over the balloon 17. See FIG. 3. Also shown there is side branch guidewire 32, indicating that the payload tracks the side branch guidewire and thus payload deployment is to take place adjacent to a side branch ostium of a bifurcated vessel. By no means is this depiction intended to restrict the scope of the present application in any way, as the payload could have been depicted as tracking the main branch guidewire, i.e.,— intended for deployment in the main branch of the bifurcation.

A unidirectional bending member 50 is located at the distal end of the catheter 10. Unidirectional bending member 50 is mounted at the distal end of shaft 11. In a specific arrangement, the proximal end of shaft 11 is constructed of a material that exhibits sufficiently high torsional flexibility so that the unidirectional bending member portion of the catheter is able to undergo the rotation necessary to orient the device. Employing an elastomeric material to construct the shaft in the area proximal to the unidirectional bending member 50 is one way to attain this result. In other arrangements, dimensions of shaft 11 can be varied in order to impart torsional flexibility in the region where the unidirectional bending element joins to the catheter. For example, the wall thickness of shaft 11 can be reduced in the area proximal to where the shaft 11 joins to the unidirectional bending member 50, or alternatively, the diameter of the shaft 11 in this region can be reduced. In yet another arrangement, the unidirectional bending member is butt welded to the end of one of the guidewire lumens 14 or 18.

Exit ports 27 and 29 for main branch and side branch guide wires are located at approximately the mid-portion of the distal payload for the side branch guidewire (not shown) and the catheter tip (35) for the main branch guidewire.

Figure 4:
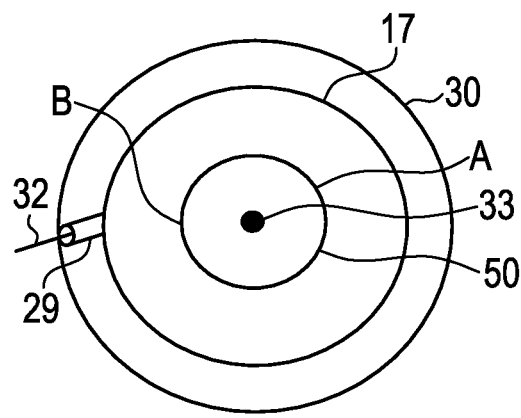
FIG. 4 is a cross sectional view of another aspect of the present invention.

As shown in FIG. 4, the unidirectional bending member 50 is coaxially arranged with the main branch guide wire 33, that is, with the guidewire arranged coaxially within unidirectional bending member 50. Unidirectional bending member 50 extends within balloon 17 and is co-located therewith for a portion of its length with balloon 17 (FIG. 1), with the stent 30 being carried over the balloon and unidirectional bending member portion. A portion of the unidirectional bending member 50 extends sufficiently distal to the payload in order to orient the device and payload for deployment. The unidirectional bending member is disposed balloon, but not fully around as that would restrict deployment.

FIGS. 5-10 show a particular embodiment of a unidirectional bending member 50 suitable for use in the present invention, which, as implied by its name, bends substantially unidirectionally. The unidirectional bending member 50 is substantially symmetrical, and more specifically as shown here, is substantially circular in its cross section. "Substantially symmetrical" as used herein refers to the cross section of the unidirectional bending member 50, at a location of generally uniform material (i.e., not at a location where the member is cut around its perimeter, or in other words, as viewed at the location where lines H-H are present in FIG. 5C), and in an unbent state, where (1) the member has substantially equal side lengths, or (2) the member has a substantially equal diameter or radius, or (3) the member is dimensioned to fit within a circle or square, such that at all of the outermost portions of the member's outer perimeter, it touches the walls of a circle or square. Such an example of (3) would be of a member having a five or six point star shape, the member fitting within a box or circle, with the points (i.e., outer perimeter) all substantially touching the walls of the circle or box, neither substantially extending beyond the walls or substantially falling short of the walls.

Further, under the conditions described above, the term "substantially symmetrical" excludes members exhibiting major and minor transverse directions, as disclosed in U.S. Pat. No. 6,544,218.

Unidirectional bending member 50, is interconnected along its length while divided into a plurality of connected segments with a laser or other suitable cutting apparatus having industrial applicability, which device makes cuts that define the segments therebetween. As shown in FIGS. 5-10, the segments are approximately of equal length, although it should be understood that unidirectional bending members having segments of varying length can be produced, and it should be understood that unique bending characteristics can result from cutting the segments into varying lengths.

Figure 5:
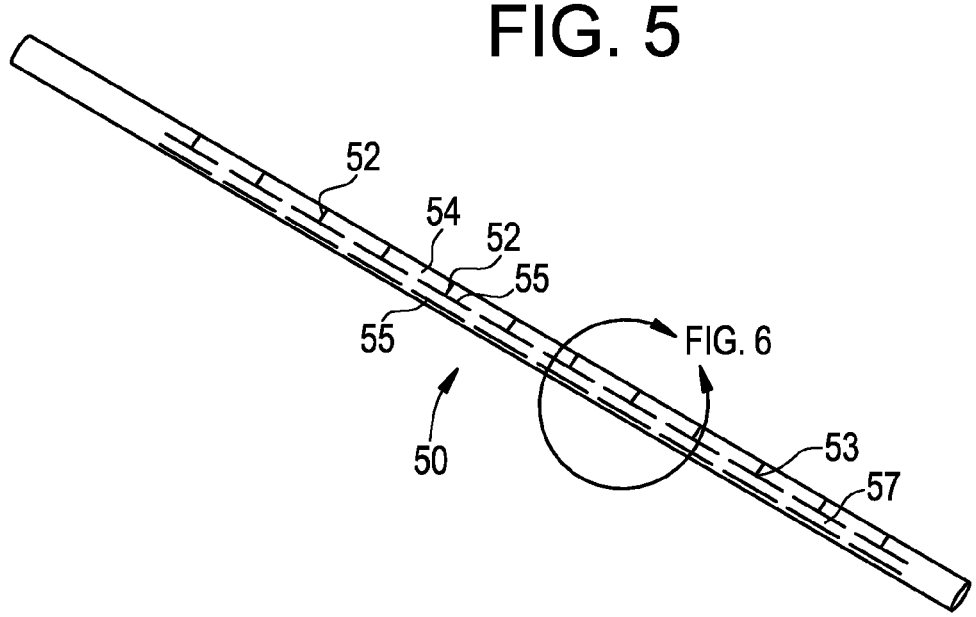
FIG. 5 is a perspective view of an embodiment of a unidirectional bending member of the present invention.
Figure 5A:
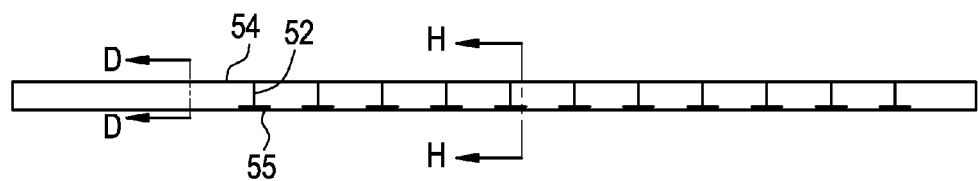
FIG. 5A is a top plan view of the unidirectional bending member shown in FIG. 5.
Figure 5B:
FIG. 5B is a cross sectional view taken along line D-D in FIG. 5A.
Figure 5C:
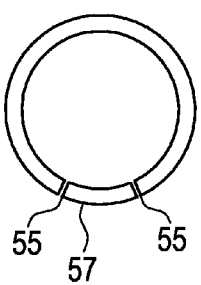
FIG. 5C is a cross sectional view taken along line H-H in FIG. 5A.
Figure 7:
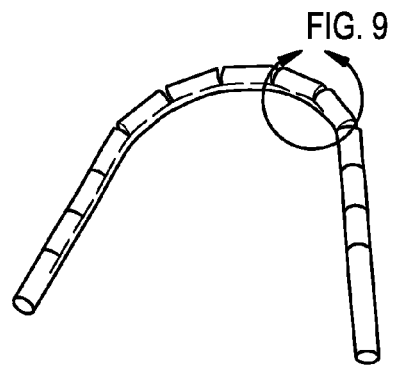
FIG. 7 is a perspective view of the embodiment shown in FIG. 5, shown while flexing.
Figure 8:
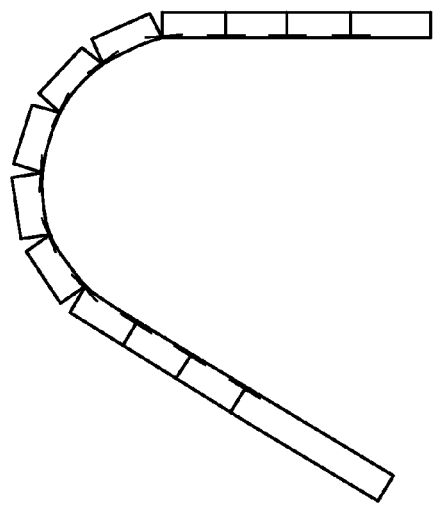
FIG. 8 is a top plan view of the embodiment shown in FIG. 5, shown while flexing.

The member segments are divided by cutting the member around its circumference at several locations. The circumferential cuts (representatively shown as 52 in the figures) define each segment 54. In the depicted embodiment, the cuts extend around a portion of the circumference of the member, and in a specific aspect of the invention, the cuts extend around a majority of the member circumference, for example, about 300° of the circumference. Uncut, or solid member portions, are present between the termini 53 of each cut. This arrangement can be viewed in FIGS. 5A, 5B, and 5C. FIG. 5B, a view taken along line D-D of FIG. 5A, where a circumferential cut has been made, shows connector portion 57, which longitudinally connects the segments of the member 50. FIG. 5C, taken along line H-H of FIG. 5A, shows a substantially solid tube arrangement, interrupted only by the second cuts 55. That is, a second cut 55 axially extends in the longitudinal direction of the member axis at the termini of each circumferentially-extending cut 52. As shown, there are a pair of second, axially extending cuts 55 for each circumferentially extending cut 52. The solid member portions between the cuts are characterizable as isthmus-like connectors 57. The isthmus-like connectors 57 maintain member interconnectedness from end to end of the member.

Figure 9:
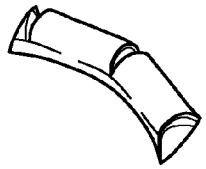
FIG. 9 is a detailed view of the embodiment shown in FIG. 5, shown while flexing.
Figure 10:
FIG. 10 is a side view of the embodiment shown in FIG. 5, shown while flexing.

As specifically shown in FIGS. 7-10, the tube flexes or bends around the isthmus-like connectors 57, thereby positioning such connectors on the interior, or short side of the bend. Likewise, the circumferential cuts 52 open during bending on the exterior, or long side, of the bend. Also, during bending, the longitudinally extending cuts 55 open slightly, as shown in FIG. 9, relieving stress at the termini 53. (In FIG. 10, a guidewire (unnumbered) can be seen through the openings the cuts 52, passing though the unidirectional bending member. In addition, the longitudinally extending cuts reduce the tendency of the tube to bend opposite to the desired direction. (That is, the longitudinally extending cuts reduce the number of circumferential cuts necessary to impart sufficient flexibility to the tube. Thus, the reduction in number of circumferential cuts can reduce the possibility of a reverse bend from occurring in the tube due to closure of the numerous gaps formed by the cuts.

In the aforedescribed arrangement, the bending member can bend only unidirectionally, that is, in only one direction, which is around the interconnections. Also, the connectors 57 are sufficiently stiff so as to prevent the tube from bending such that interconnections are positioned on the long side of the bend, which is undesirable.

The manner in which the unidirectional bending member 50 bends facilitates orientation of the device as it travels through (1) curves or bifurcations in the vessel, (2) curves or bends in the guidewire, or (3) other eccentricities located within the vessel that force the tube into a curved path. So long as the unidirectional bending member possesses a sufficient degree of freedom to rotate, it will assume the path of least resistance as it travels through the vessel, and thereby rotate/orient itself to conform to the bend in the path of the unidirectional bending member.

By way of alternative, the tube of the embodiments shown in FIGS. 5-10 can be provided with a longitudinal cut that runs for substantially the entire length of the tube. While a longitudinal cut need not be present on the tube, and thus is not necessary to the invention, the provision of the longitudinal slot reduces the extent to which the tube is cut circumferentially as well as the number of circumferential cuts required. Thus, providing a longitudinal cut can result in improved production efficiency.

Figure 11:
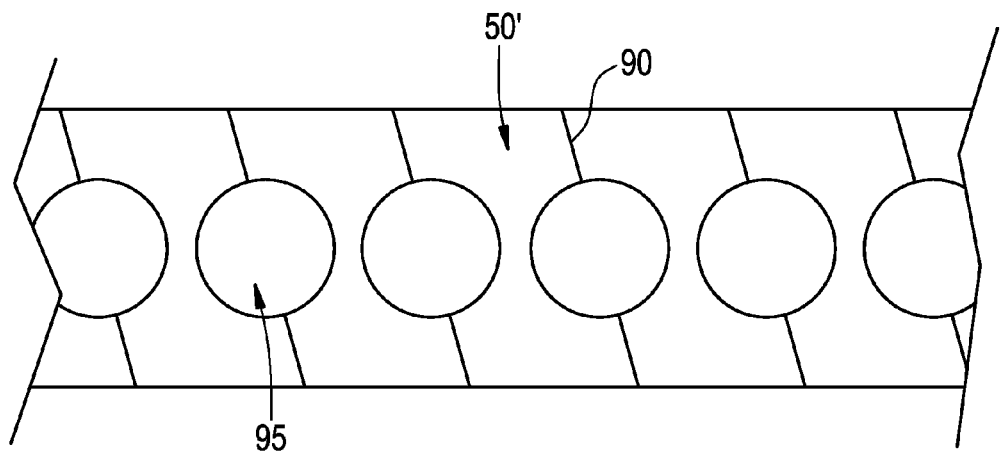
FIG. 11 is a perspective view of an alternative embodiment of a unidirectional bending member of the present invention.

In a further unidirectional bending member embodiment, an arrangement similar to the laser cut tube can be provided by forming a tube from a welded segment of a helical coil, as shown in FIG. 11. That is, the tube 50' is cut helically, akin to a coiled ribbon, and the spaces between the helical cuts 90 are welded closed with solder or the like (numerically designated as 95) on one continuous, axially extending segment, located on one tube side. The welds link together adjacent turns of the helix. As with the aforedescribed arrangements, the tube flexes or bends around the welds, thereby positioning such connectors along the inside of the bend. The outside of the tube opens along the helical cut that wraps around the circumference of the tube.

In one particular aspect of the present invention, the segments are formed from spring segments that are welded together.

Figure 12:
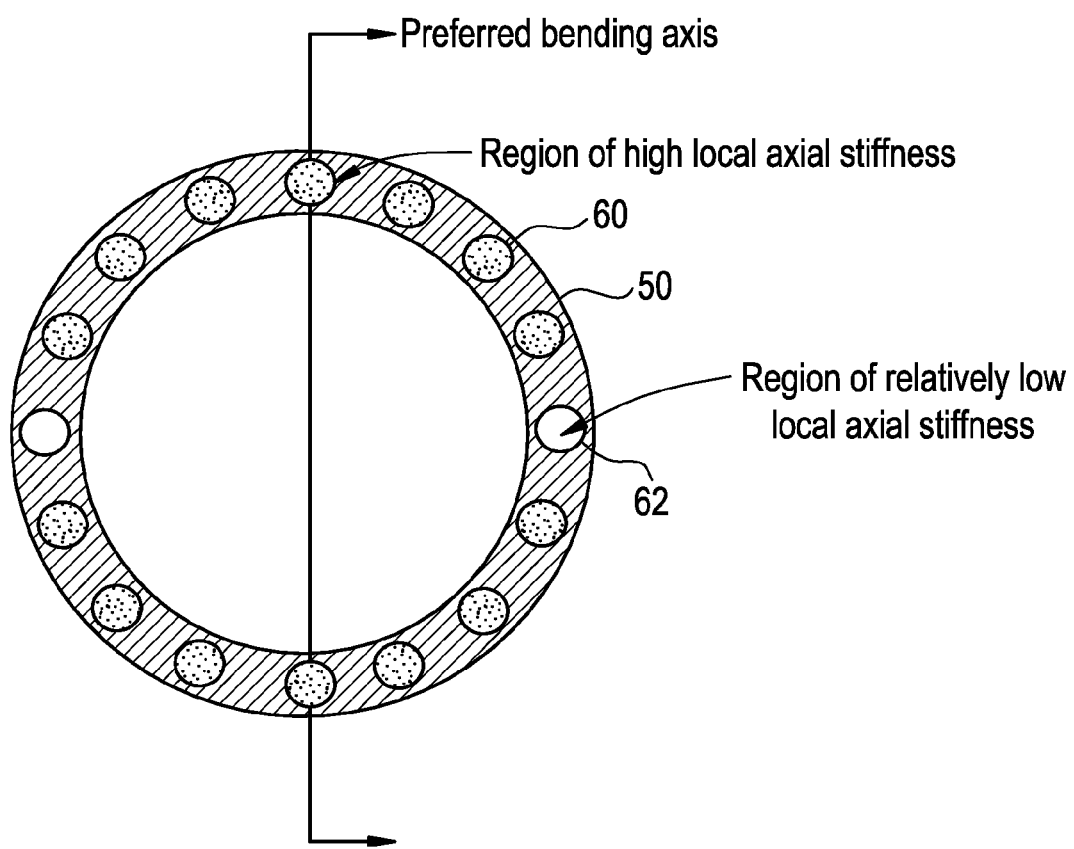
FIG. 12 is a cross-sectional view of an alternative embodiment of a unidirectional bending member of the present invention.
Figure 13:
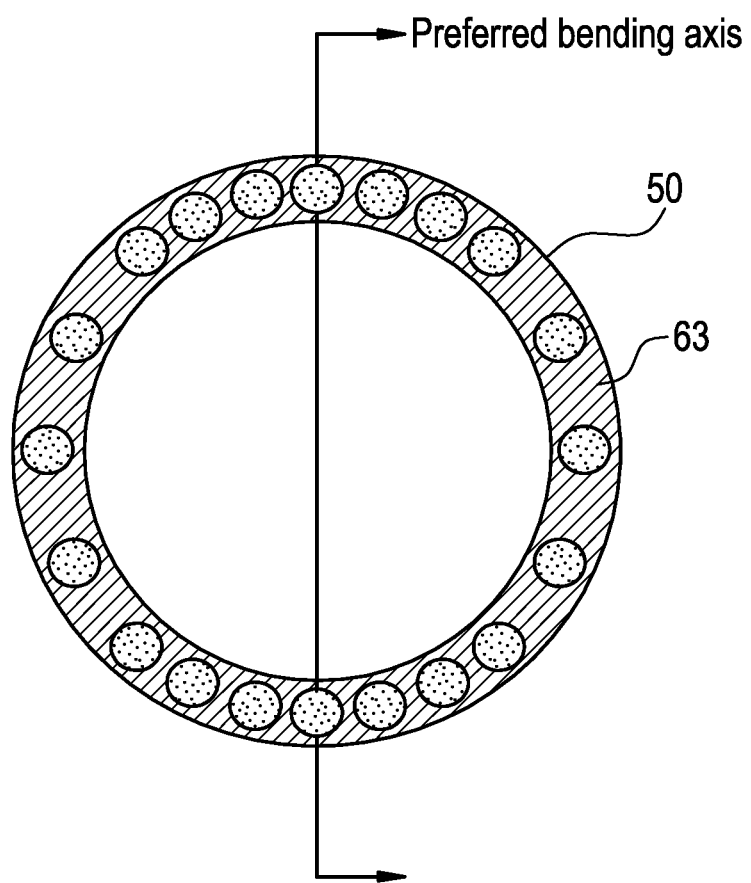
FIG. 13 is a cross-sectional view of yet another alternative embodiment of a unidirectional bending member of the present invention.

In yet another arrangement, the unidirectional bending member need not be provided with cuts and connectors, but instead can be configured of a non-segmented tube in which unidirectional flex capability is imparted by embedding a component within the tube wall to arrange for a preferred direction of bending. Alternatively, the component can be positioned on the surface of the tube to effect the preferred direction of bending. For example, as shown in FIG. 12, a fibrous material 60 can be embedded within the wall of the tube over at least a portion of the circumference and length thereof. The tube will exhibit greater stiffness in the regions where such fibers are embedded, when the embedded fibrous material is a stiffness-imparting material. Such a stiffness-imparting material 60 could be an array of metal wires, thereby resisting bending in the direction extending across the axis of the fibers. Conversely, in regions 62 where no fibers are present, or regions 63 where only a relatively small number of fibers are present (see FIG. 13), then the tube will exhibit an inclination to bend across the tube in such regions. It should be understood that where the density of the stiffness imparting fibers is relatively high, then greater stiffness would be exhibited in that region. In yet another arrangement, shown in FIG. 13, the fibers are embedded in the wall of the tube around its circumference; however, the density of such fiber varies around the circumference, so that segments of the tube circumference having a fibrous density less than other segments of the tube exhibit a tendency to flex. When at least two of such segments having a lesser fibrous density are aligned across the tube from each other, then the tube shall exhibit a preference to bend and flex through those regions of lesser fiber density.

Figure 14A:
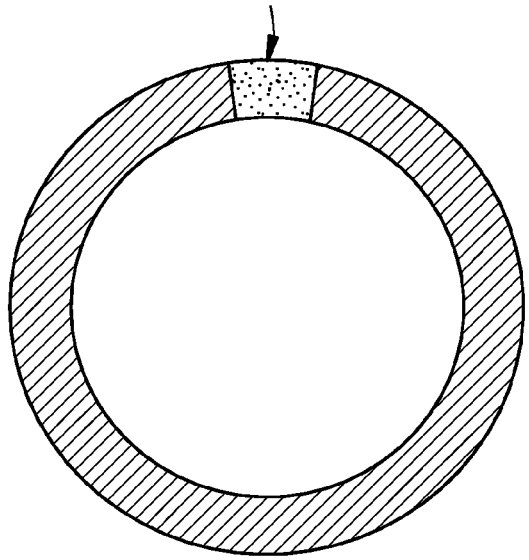
FIGS. 14A-14F are cross-sectional views of additional embodiments of a unidirectional bending member of the present invention.
Figure 14B:
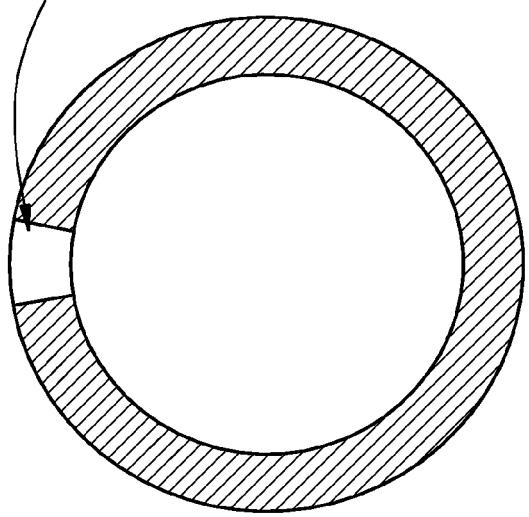
Figure 14C:
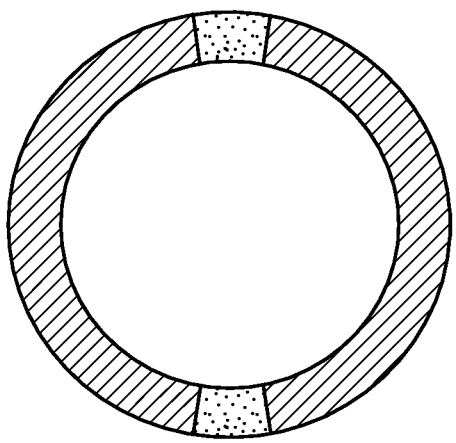
Figure 14D:
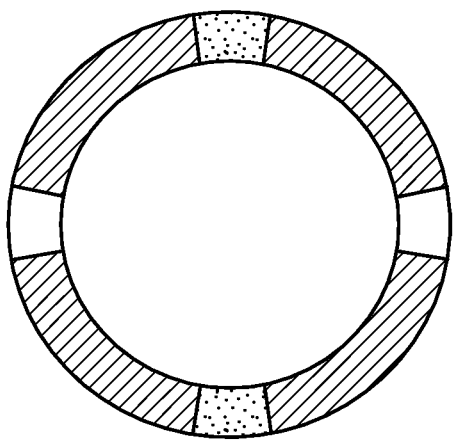
Figure 14E:
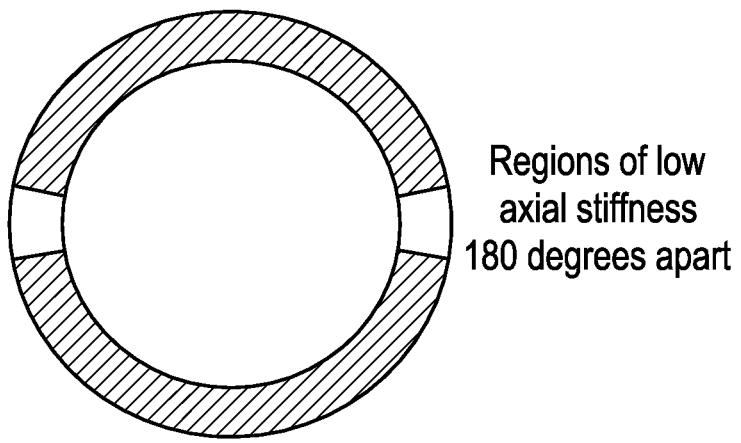
Figure 14F:
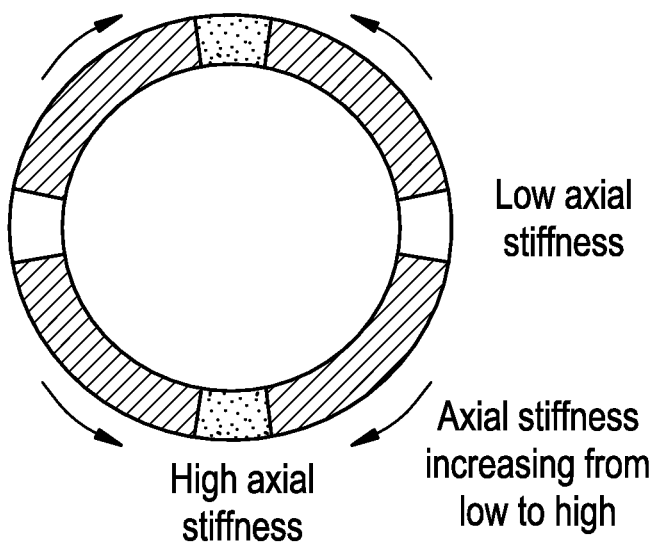

FIGS. 14A-14F illustrate additional embodiments of the unidirectional bending member. In FIG. 14A, the unidirectional bending member is provided with a single region of high axial stiffness in relation to the remainder of the circumference. In FIG. 14B, the tube is provided with a single region of low axial stiffness in relation to the remainder of the circumference. FIG. 14C shows a tube in which regions of high axial stiffness are positioned 180° apart from each other. FIG. 14D shows a tube in which regions of high and low axial stiffness alternate at 90° orientations. FIG. 14E shows a tube in which regions of low axial stiffness are positioned 180° apart from each other. FIG. 14F shows a tube in which axial stiffness increases from high to low (or vice versa) as tube circumference is traversed.

Figure 15:
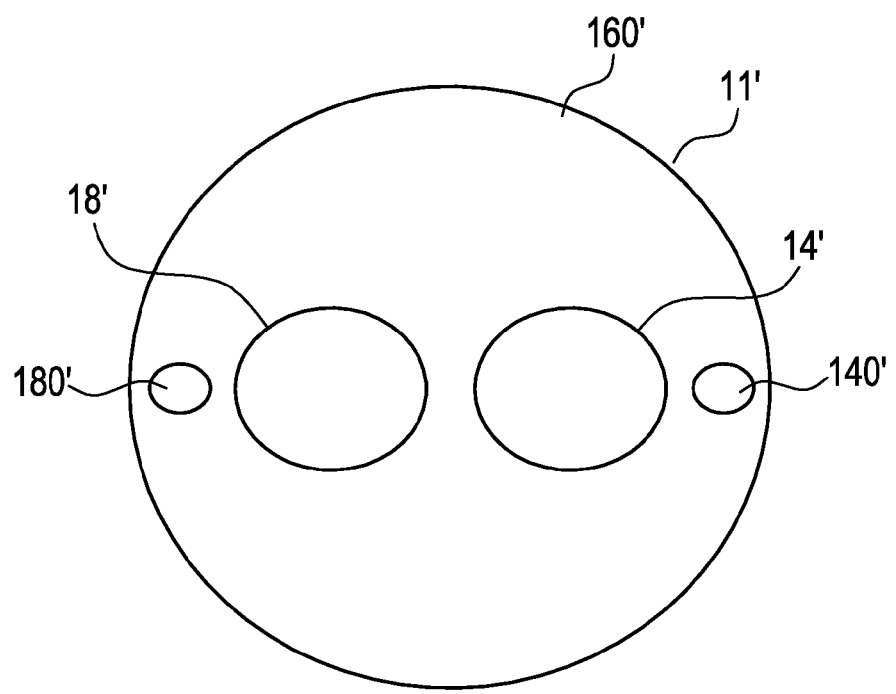
FIG. 15 is a cross-sectional view of an alternative embodiment of a unidirectional bending member of the present invention.

In yet another exemplary embodiment, shown in FIG. 15 the unidirectional bending member 50 can be made to bend in a preferred direction by providing a shaft 11' in which a preferential bending direction is created by positioning and configuring the internal lumens 14' and 18', 140' and 180' within walls 160' of shaft 11' to provide for a preferred bending direction of the outer tube. For example, the lumens can be arranged around the inner circumference of the outer tube to provide flexibility in a desired direction. If such tubes provide stiffness, then the unidirectional bending member would be constrained against bending through the inner tubes. However, by selectively omitting an inner tube from a location along the inner circumference would remove constraint against bending through that location, and hence create a preferred direction through which the tube can bend.

Also, chemical, electrical or mechanical means can be used to modify unidirectional bending member stiffness so the unidirectional bending member can be transversely displaced, resulting in a preferred bending orientation. Material phase changes, changes in modulus, or changes in yield stress can be electrically induced in the tube in order to create a preferred bending direction and orientation. Likewise, a component can be present in the unidirectional bending member construction for inducing an axial shift or displacement in the device.

Figure 16:
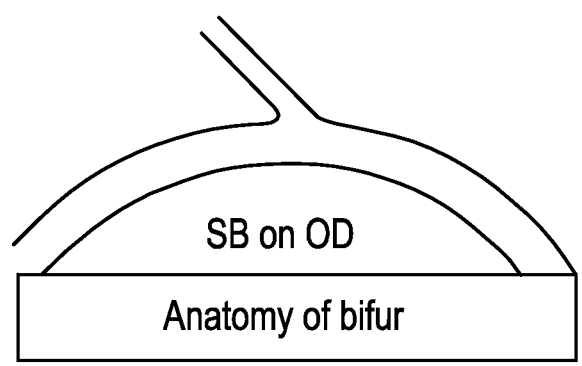
FIG. 16 is a cross sectional view of a first bifurcation configuration in a patient's vasculature.
Figure 17:
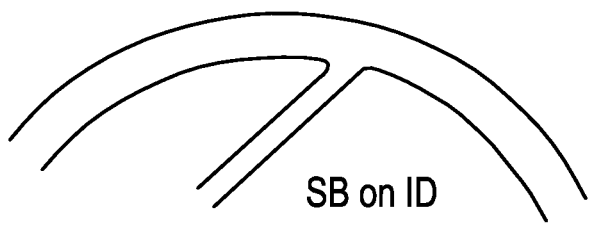
FIG. 17 is a cross sectional view of a second bifurcation configuration in a patient's vasculature.

FIG. 16 illustrates a vessel anatomy having a main branch bend and a side branch off the outside of the main branch bend. FIG. 17 illustrates a vessel anatomy having a main branch bend and a side branch off the inside bend on the main branch. It should be understood that the device of claim 1, utilizing the unidirectional bending member embodiments of FIGS. 5-15, can deploy a payload, such as a stent, to different branch arrangements, such as the ones shown above. That is, the unidirectional bending member can be oriented, via tube rotation, to deploy payload facing (or properly oriented with respect to) the side branch ostium, regardless of whether the side branch is positioned on the inside or outside of the bend in the vessel.

Specifically, as shown in FIG. 4, an arrangement is shown that is well suited for delivery of payload to the main branch of a bifurcated vessel. In this case, the unidirectional bending member 50 is carried over the main branch guide wire 33, with both main branch guide wire 33 and unidirectional bending member 50 passing through the balloon 17 (provided with appropriate lumen for guidewire). Further, stent 30 is carried over these components. At around the midpoint of the stent 30, the side branch guide wire 32 exits through the side branch guide wire exit port 29 and passes through the side wall of the stent 30, and into side branch of the bifurcated vessel.

The catheter can be properly oriented when the unidirectional bending member at the distal end of the catheter bends and rotates (as necessary), as the unidirectional bending member passes through the vessel bend. The device configures itself when the unidirectional bending member rotates, with the stent for deployment in the main branch and the side branch guidewire exit port orient to face the side branch ostium, so the side branch guidewire can be passed into the side branch.

As shown in FIG. 4, and drawing upon the embodiments of FIGS. 5-10, A denotes the location on the unidirectional bending member 50 where the member is interconnected, such as by connections 57. B denotes the location where the unidirectional bending member 50 is open (i.e.—element 52 previously discussed). Thus, in this particular orientation of the device, mindful that in FIG. 4 the proximal end of the member 50 is coming out of the page, the member will bend rightward, with side branch guidewire positioned to extend into a side branch on the outside of the bend, as depicted in FIG. 15.

Figure 4A:
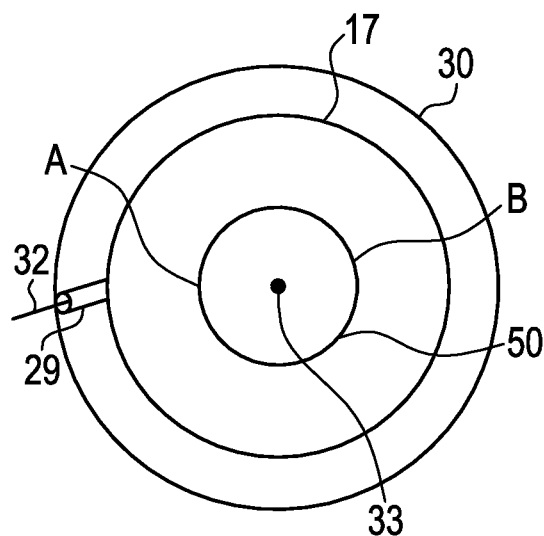
FIG. 4A is a cross sectional view of another aspect of the present invention.

FIG. 4A shows what is essentially the opposite of the FIG. 4 arrangement, in which the tube has oriented itself with the connected side A on the left side of the figure, and the open side B on the right side of the figure. In this particular orientation of the device, with the proximal end of the member 50 coming out of the page, the member will bend leftward, with side branch guidewire positioned to extend into a side branch on the inside of the bend, as depicted in FIG. 16.

Figure 4B:
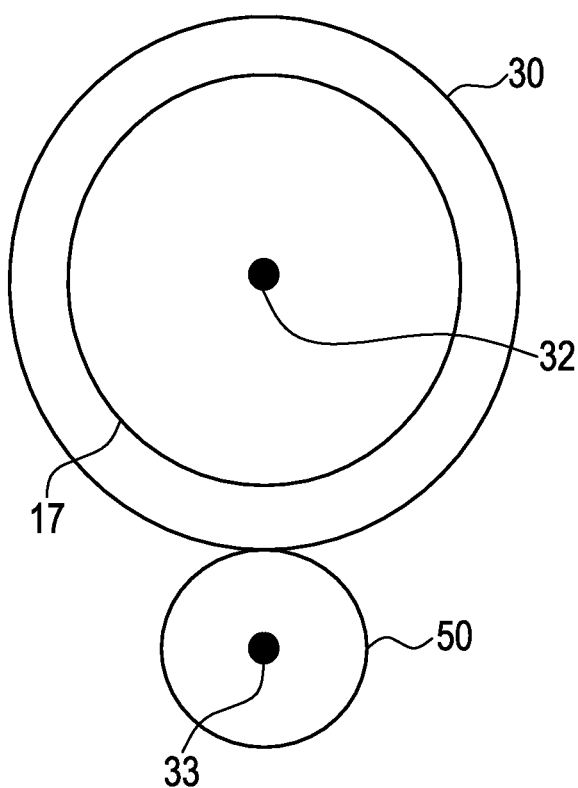
FIG. 4B is a cross sectional view of another aspect of the present invention.
Figure 6:
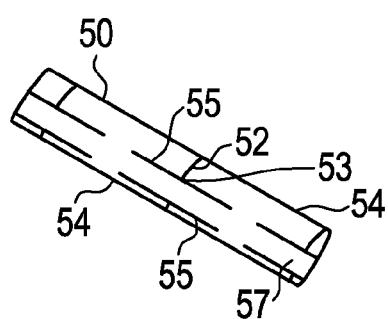
FIG. 6 is a detailed view of the embodiment shown in FIG. 5.

Furthermore, is readily appreciable that implantation within the side branch can be similarly achieved, owing to the versatility of the device. For example, as shown in FIG. 4B, by passing the main branch guide wire 33 through the flex tube 50 (with same positioned exterior to the payload), with the balloon 17 and side branch guidewire 32 within the payload (stent) 36, the device can be properly oriented by allowing the flex tube to rotate the distal end of the device as the flex tube passes through the bend in the vessel. With this arrangement, the stent can be passed into the ostium of the side branch and then deployed in the side branch.

It will be understood that this disclosure, in many respects, is only illustrative. Changes may be made in details, particularly in matters of shape, size, material, and arrangement of parts without exceeding the scope of the invention. Accordingly, the scope of the invention is as defined in the language of the appended claims.

What is claimed is:

1. A percutaneously introducible catheter device for carrying a medically useful payload positioned upon the device to a location of interest in a conduit of a patient, comprising:
   an intralumenal element sized and dimensioned to travel to a location of interest in a conduit of a patient;

a flexible, tubular element positioned and coaxially arranged at a distal end of the intralumenal element wherein the flexible element exhibits the capability to bend substantially unidirectionally, the flexible, tubular element is substantially circular in cross section and is divided into a plurality of equally sized connected segments formed by a series of equal circumferential cuts extending about 300 degrees up to pairs of termini cuts that extend in the longitudinal direction creating equal T shaped cuts thereby forming equal isthmus like connector elements between the cuts, the combination of the circumferential cuts and the T-shaped configuration resulting from the termini cuts are configured to ensure bending in only one direction;

wherein the flexible element, when encountering a non-linear path bends in the permitted direction in conformance to the non-linear path.

2. The device of claim 1 wherein the payload is selected from the group consisting of a diagnostic tool, ultrasound transducer (IVUS), pressure transducer, infrared sensor and endoscope lens.

3. The device of claim 1 wherein the payload is selected from the group consisting of a therapeutic device, a stent, an atherectomy device, brachytherapy source, herniated or focal bump balloon, injectable needle, laser and thermal cauterization device.

* * * * *

UNITED STATES PATENT AND TRADEMARK OFFICE
CERTIFICATE OF CORRECTION

| | | Page 1 of 1 |
|---|---|---|
| PATENT NO. | : 8,518,052 B2 | |
| APPLICATION NO. | : 11/488401 | |
| DATED | : August 27, 2013 | |
| INVENTOR(S) | : Burgermeister et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1380 days.

Signed and Sealed this
Seventeenth Day of February, 2015

Michelle K. Lee
*Deputy Director of the United States Patent and Trademark Office*